(12) United States Patent
Lintner

(10) Patent No.: US 6,620,419 B1
(45) Date of Patent: Sep. 16, 2003

(54) COSMETIC OR DERMOPHARMACEUTICAL USE OF PEPTIDES FOR HEALING, HYDRATING AND IMPROVING SKIN APPEARANCE DURING NATURAL OR INDUCED AGEING (HELIODERMIA, POLLUTION)

(75) Inventor: Karl Lintner, Rambouillet (FR)

(73) Assignee: Sederma, Le Perray en Yvelines (FR)

( * ) Notice: Subject to any disclaimer, the term of this patent is extended or adjusted under 35 U.S.C. 154(b) by 0 days.

(21) Appl. No.: 09/787,175

(22) PCT Filed: Sep. 13, 1999

(86) PCT No.: PCT/FR99/02178
§ 371 (c)(1), (2), (4) Date: Mar. 15, 2001

(87) PCT Pub. No.: WO00/15188
PCT Pub. Date: Mar. 23, 2000

(30) Foreign Application Priority Data

Sep. 15, 1998 (FR) .............................................. 98 11533

(51) Int. Cl.[7] .............................. A61K 6/00; A61K 7/00; A61K 31/74; A61K 38/00; A01N 37/18
(52) U.S. Cl. ........................ 424/401; 424/78.03; 514/2; 530/328; 530/329; 530/330
(58) Field of Search .............................. 424/401, 78.03; 514/2; 530/328, 329, 330

(56) References Cited

U.S. PATENT DOCUMENTS 4,640,943 A * 2/1987 Meguro et al. ............. 523/200
5,171,577 A * 12/1992 Griat et al. ................. 424/450
5,458,881 A * 10/1995 Berger et al. ............... 424/401
5,498,420 A * 3/1996 Mentrup Edgar et al. .. 424/450

OTHER PUBLICATIONS

XP–002106610, Kou Katayama et al., "*A Pentapeptide from Type I Procollagen Promotes Extracellular Matrix Production*", 12/92, ppgs. 9941–9943.

* cited by examiner

Primary Examiner—Sreeni Padmanabhan
Assistant Examiner—Lauren Q. Wells
(74) Attorney, Agent, or Firm—Young & Thompson

(57) ABSTRACT

The invention concerns the use of peptides of general sequence X-Thr-Thr-Lys-Y, wherein in particular X=lysine and Y=serine, in cosmetic or dermopharmaceutical compositions. It is moreover advantageous to use said peptides in mutual combination. In order to enhance their activity and their stability, the peptides are chemically modified to increase their lipophilicity, by grafting on the N-terminal amine of X, either a fatty acid chain, or by esterification or amidation of the C-terminal carboxyl group of Y. The peptides can be obtained by synthesis, biotechnology or controlled hydrolysis or plant proteins. The resulting compositions are advantageously used for stimulating healing, hydrating or all skin treatments. They are particularly active against formation or deterioration of wrinkles and against all the consequences of skin ageing, whether natural or induced (heliodermia, pollution), as well as for dry skin.

16 Claims, No Drawings

COSMETIC OR DERMOPHARMACEUTICAL USE OF PEPTIDES FOR HEALING, HYDRATING AND IMPROVING SKIN APPEARANCE DURING NATURAL OR INDUCED AGEING (HELIODERMIA, POLLUTION)

This is U.S. National Stage Application of PCT/FR99/02178 filed Apr. 13, 1999, now WO 00/15188 published Mar. 23, 2000.

Aging, particularly of the skin, involves important intimate tissue biochemical disturbances which are manifested by macroscopic modifications, conventionally judged to be undesirable, and which continuously preoccupy both women and men.

Suntanning with natural solar UV, or artificially in beauty salons, is responsible for cutaneous aging well known to dermatologists under the name heliodermia (Dr. C. Musy-Preault, (1994) *The Maladies of the Skin*, Albin Michel ed., Paris).

Other components of our present way of life, such as physical and chemical aggression by pollution; the consumption of alcohol and tobacco, promote and aggravate the aging processes.

Moreover, in the course of private or professional life, the skin, first barrier of the organism against the outside world, is menaced in its integrity by numerous localized aggressions such as cuts, burns, inflammatory reactions. To correct these, the organism has developed a series of reactions, complex and overlapping each other: healing.

The cosmetic industry is continuously searching for new ingredients capable of countering the effects of aging in general and/or promoting cutaneous healing.

To do this, one of the possible approaches consists in promoting the tissue restructuring by neosynthesis of the different elements constituting the skin. Just as cement ensures the cohesion of bricks in a wall and gives it its solidity, the different types of collagens and other mucupolysaccharides, are the constituent elements of cutaneous tissue.

Promoting the synthesis and the incorporation of these molecules is surely necessary but not sufficient by itself. It is also necessary to prepare the terrain by giving it a good basis on which the mechanisms of healing can carry out lasting repairs. In the situations described above, this basis is the extracellular matrix, which is known as the basal layer when it is located at the interface of the epithelium and conjunctive tissue. Improvement or reconstruction of the extracellular matrix is important because it is now known that not only this structure plays "the role of framework stabilizing the physical structure of the tissues" but it also "plays a role . . . in the regulation of the behavior of the cells which are in contact with it—influencing their development, their migration, their proliferization, their form and their functions" (Molecular Biology of the Cell, 3rd edition Medicine-Science, Flammarion, Paris, page 972).

There is accordingly a special interest in two of the principal constituents of this extracellular matrix: the collagens and the glycosaminoglycans (also known as GAGS).

In the framework of this patent, the effects of aging on the collagens and the glycosaminoglycans can be summarized as:

The decrease of synthesis of these molecules by fibroblasts, decrease due to the conjunction of two causes: on the one hand the quantity of renewal of these productive cells decreases with age and, on the other hand the quantity of molecules secreted by these cells also decreases.

When it is considered that collagen represents about 80% of the cutaneous proteins, it is easy to understand that the slightest decrease in its tissue concentration can have important consequences on the mechanical and physiological properties of the skin.

The glycosaminoglycans are capable of fixing large quantities of water. The decrease of their tissue concentration thus gives rise to cutaneous dehydration.

The appearance of structural modifications of the neo-synthesized molecules which leads to the reticulation of the fibers and hence their rigidification.

For collagen, the variations of the a chains modify the distribution of these different forms. For example, the proportion of type III collagen increases in the epidermis when the type IV collagen accumulates in the basal membrane. There have also been observed the appearance of reactions, enzymatic or not (of the Maillard reaction type) which create connections, called crossings, either between two fibers of collagen, or between the collagen itself and glucose molecules, thereby rigidifying the networks of collagen fibers.

Aging manifests itself in the glycosaminoglycans by the imperfect synthesis of their polysaccharide chains and by a decrease in their sulfation. More than with collagens, the radical forms of oxygen degrade the GAGs in an irreversible manner.

The skin thus loses its substance by the decrease in the quantity of its constituents, hardens by the loss of elasticity of the collagen fibers and by dehydration.

All this contributes to giving the aged skin its characteristic appearance: dryness, absence of flexibility, fineness, fragility, more or less numerous wrinkles that are more or less deep.

Healing itself requires, at least partially, similar needs because it is necessary to reconstruct and hence to produce a tissue mass; this implies locally, the increased synthesis of the different cutaneous constituents.

Thus, any product capable of inducing one or more processes increasing locally the synthesis of collagens and glycosaminoglycans, will permit obtaining the effect sought by all those who wish to reduce the cutaneous marks of aging as well as those wishing to improve healing, not only to quicken it but also for the aesthetics and quality of the result.

The invention which is the object of this patent application resides in the fact that we have developed a product which responds to the preceding criteria and of which we have demonstrated the efficacy, in vitro and in vivo, by sophisticated scientific tests.

It is known that the synthesis of collagen can be stimulated (in vitro), in cell cultures, by the C-terminal fragment of collagen I which constitutes the peptide Lys-Thr-S Thr-Lys-Ser (Katayama K. et al., *Journal of Biological Chemistry* (1993), 259:9941–9944.

Moreover, it is possible to increase the synthesis of the cutaneous glycosaminoglycans by vegetal extracts (for example, in the rat: Chithra P. et al., *Journal of Ethnopharmacology* (1998), 59:179–186).

Our patent application rests on the discovery, that when administered, alone or in combination with each other, by topical route in vivo, and hence by a method suitable for cosmetics, the peptides of the general formula $R_1$-X-Thr-Thr-Lys-$(AA)_n$-Y and their salts, wherein:

X representing a basic amino acid of D or L orientation (lysine, arginine, histidine, ornithine, citrulline, sarcosine, statine), $(AA)_n$ representing a chain of n amino acids, natural or not, with n varying from 0 to 5, R₁ being H or a fatty acid chain of 2 to 22 carbons, hydroxylated or not, saturated or not, linear or branched, sulfurated or not, cyclic or not, or a biotin group, or a protective group of the urethane type used in peptide synthesis such as the groups benzyloxycarbonyl (Z), terbutyloxycarbonyl (tBoc), fluorenylmethyloxycarbonyl (Fmoc), allyloxycarbonyl (Alloc)

Y=OR₂ or NR₂R₃ wherein R₂ and/or R₃ are a hydrogen atom or an aliphatic or aromatic chain of 1 to 22 carbons, hydroxylated or not, saturated or not, linear or branched, sulfurated or not, cyclic or not, except peptides wherein R₁=H and X=Lys and Y=OH and with n=0 or (AA)ₙ=Ser when n=1, are capable of increasing in a substantial way the concomitant synthesis of collagen and glycosiminoglycans and that this fact permits obtaining a synergetic effect because thus, the observed result is greater than could be hoped for from the addition of each of its effects.

Thus, the newly-formed collagen fibers overlay each other immediately in the trellis of the glycosiminoglycans of the basal layer newly synthesized; thereby accelerating the process of cutaneous regeneration as well as the mean level of tissue hydration.

The peptides preferably used in this way can be characterized in that n=1, R₁ is a fatty acid chain of 2 to 22 carbons and Y is OH or NH₂, and more precisely with X=lysine, (AA)ₙ=serine, R₁=the palmitoyl group and Y=OH.

The peptides which are the objects of this application can be obtained either by conventional chemical synthesis (in heterogenous phase or homogeneous phase), or by enzymatic synthesis (Kullman et al., J. Biol. Chem. 1980, 255, 8234) from constituent amino acids or their derivatives.

The small size of these peptides permits making them by industrial synthesis, at a good cost. Their demonstrated high activity permits the commercial use of them in a large number of cosmetic or dermopharmaceutical products that are financially favorable.

The peptide can be obtained also by fermentation of a strain of bacteria, modified or not by genetic engineering, to produce the sought sequences or their different fragments.

Finally, the peptide can be obtained by extraction of proteins of animal or vegetable origin, preferably vegetable, adapted to contain these sequences in their structure, followed by controlled hydrolysis, enzymatic or not, which frees the peptide fragments in question (of the sequence X-Thr-Thr-Lys-(AA) preferably Lys-Thr-Thr-Lys-Ser), of a mean size comprised between 300 and 2000 daltons, with the stipulation that the freed fragments correspond to the preceding peptide synthesis in plants which are adapted to contain these sequences within their structure. The managed hydrolysis permits freeing these peptide fragments.

To carry out the invention, it is possible but not necessary, either to extract the proteins in question first and then to hydrolyze them, or to carry out hydrolysis first on a raw extract and to purify the peptide fragments. There can also be used the hydrolysate without extracting from it the peptide fragments in question, by ensuring however the stopping of the enzynamic hydrolysis reaction timewise and determining the presence of the peptides in question by suitable analytic means (radioactivity tracing, immunofluorescence or immunoprecipitation with specific antibodies, etc.).

Other simpler or more complex processes, leading to less costly or more pure products, are easily envisagable by those skilled in the art knowing the extraction and purification procedures for proteins and peptides.

By way of example illustrating the invention, there will be cited several cosmetic formulations representative but not limiting, of the invention:

EXAMPLE NO. 1

Gel

| | |
|---|---|
| Carbopol 1342 ® | 0.3 |
| Propylene glycol | 2.0 |
| Glycerine | 1.0 |
| White petroleum jelly | 1.5 |
| Cyclomethicone | 6.0 |
| Cetyl alcohol | 0.5 |
| Lubrajel ® MS | 10 |
| Triethanolamine | 0.3 |
| N-Palmitoyl-Sarcosine-Lys-Thr-Thr-Lys-Ser | 0.0005 |
| Water, preservatives, perfume qsp | 100 g. |

EXAMPLE NO. 2

Cream

| | |
|---|---|
| Volpo S20 | 2.4 |
| Volpo S2 | 2.6 |
| Prostearyl 15 | 8.0 |
| Beeswax | 0.5 |
| Abil ® ZP 2434 | 3.0 |
| Propylene glycol | 3.0 |
| Carbopol ® 941 | 0.25 |
| Triethanolamine | 0.25 |
| N-Palmitoyl-Lys-Thr-Thr-Lys-Ser | 0.25 |
| Water, preservatives, perfumes qsp | 100 g |

The activities described at the beginning of this application are illustrated by the following examples.

EXAMPLE NO. 3

Increase in Synthesis of Collagen: in vitro

The method chosen is a modification of that described by Augustin C. et al. (*Skin Pharmacol.* (1997); 10:63–70) in that we have used explants of human skin instead of human pulmonary fibroblasts, so as to render our results directly usable in cosmetology.

These explants, from abdominal or mammary plastic surgery, are incubated for 72 hours in the presence ³H-proline, with peptide N-Palmitoyl-Sarcosine-Thr-Thr-Lys-Ser, to three final concentrations in the culture medium ($2.10^{-4}\%$, $4.10^{-4}\%$ and $8.10^{-4}\%$; namely, 2, 4 and 8 ppm). The explants are then washed, the derma and epiderma of each explant are separated, homogenized and lysed. The measurement of the incorporation of ³H-proline is thus carried out in each lysat. Tests were done in triplicate.

In parallel, negative controls are carried out under the same conditions but in the absence of the peptide. Positive controls, themselves, are carried out by replacing the peptide tested by vitamin C.

In the presence of 2, 4 or 8 ppm of peptide, the incorporation of ³H-proline, which translates the synthesis of collagen, is augmented by respectively 30.2 (±2)%, 54.7 (±5)% and 90.9 (±5)% relative to that which is used in the blank tests (without peptide).

Under the same conditions, the reference product, ascorbic acid, at a concentration of 0.5mM, increases the collagen synthesis by 61.4 (±5)%.

EXAMPLE NO. 4

Increase of the Synthesis of Glycosaminoclvcans: in vitro

The same protocol as in Example No. 3 is used, except that, on the one hand, the incubation is carried out in the presence of $^3$H-glucosamine instead of $^3$H-proline and vitamin A acid is used as reference product in place of vitamin C.

In the presence of 2, 4 or 8 ppm of the peptide Lys-Thr-Thr-Lys-Ser-Ala, the incorporation of $^3$H-glucosamine which translates to synthesis of GAGs, is increased by respectively 24.5 (±3)%, 48.8 (±3)% and 67.9 (±5)% relative to that found in the blank experiments (without peptide).

Under the same conditions, the reference product, vitamin A acid, at a concentration of 100 nM, increases the synthesis of GAGs by 45.3 (±2)%.

The results obtained in these two examples clearly demonstrate a concentration dependent effect of the peptide on the synthesis of the two constituents of the extracellular matrix.

EXAMPLE NO. 5

Cutaneous Toning Activity: in vitro

For 24 hours, human fibroblasts from the same cellular culture are placed in the presence of the standard culture medium, supplemented or not for controls, with given concentrations of peptide (2, 4 and 8 ppm).

The stimulation of the synthesis of proteins is evaluated by colorimetry (so-called Biuret reaction).

To standardize the results, the quantity of proteins measured is expressed for 1000 cells present in the test.

Relative to the controlled experiments, in the presence either of 2, 4 or 8 ppm of peptide N-palmytoyl-Lys-Thr-Thr-Lys-Ser, the increase in the concentration of proteins is respectively 14.7 (±1.0)%, 21.0(±2.4)% and 44.8(±1.0)%.

Thus, this in vitro test demonstrates the concentration-dependent stimulating potential at the cutaneous level, of the peptide, which effect is directly connected to toning and thickening of skin that is too fine.

EXAMPLE NO. 6

Anti-Wrinkle Activity: in vivo

This example relates to the anti-wrinkle effect obtained, in vivo, on a panel constituted by 15 feminine adult volunteers, aged 35 to 63. The anti-wrinkle power of the cream of example No. 2, containing N-Palmitoyl-Lys-Thr-Thr-Lys-Ser at a concentration of 0.005% (namely 50 ppm), is compared to that of a placebo cream (the same cream without the active ingredient). The creams are applied to precisely identified sites, located at the corner of the left or right eye, according to a randomized distribution, twice a day, for 28 days. The parameter measured is the cutaneous relief, at the level of the contour of the eye (wrinkles called crow's feet). The quantification of the different variables of the relief is carried out by video computer analysis of silicone impressions taken at the surface of the skin according to procedures described by Corcuff et al. (1985, Int. J. Cosm. Sci. 7:117–126) and Corcuff et al. (1995, in Handbook of non-invasive methods and the skin, Serup & Jemec eds., CRC Press: 89–96).

The table below indicates the different, in percentage, of the mean values obtained between T+28 days and T0 for the mean depth of the principal wrinkle (column A) or for all of the folds (column B); for the density of the principal folds (column C) as well as for the measurement of rugosity (column D).

|         | A     | B     | C     | D     |
|---------|-------|-------|-------|-------|
| Placebo | 0.2   | +0.5  | −1.1  | +2.7  |
| Peptide | −18.2 | −21.1 | −36.9 | −21.3 |

The cream containing the N-Palmitoyl-Lys-Thr-Thr-Lys-Ser described above shows clearly a powerful anti-wrinkle effect because there is observed a large different beginning the beginning and end of the study in vivo and this for all the four parameters conventionally used in this indication.

It is to be noted that, under the same experimental conditions, the placebo cream had no effect if N-Palmitoyl-Lys-Thr-Thr-Lys-Ser was not incorporated in it, which demonstrates clearly that it is only the peptide which is the object of this patent to which can be ascribed the beneficial effect observed.

It is particularly advantageous to use these peptides in combination with each other.

The peptides of this patent can be obtained by chemical synthesis, by enzymatic means, by fermentation, by extraction of proteins of vegetable origin, by conventional peptide synthesis in homogeneous or heterogeneous phase or by enzymatic synthesis from constituent amino acids.

The peptides of this patent can be obtained by extraction of plant protein, followed by hydrolysis, enzymatic or non-enzymatic, so as to generate peptide fragments of a mean size comprised between 300 and 2000 daltons, a portion of the freed fragments containing the sequence X-Thr-Thr-Lys-(AA)$_n$, preferably the sequence Lys-Thr-Thr-Lys-Ser.

The peptides of this patent, alone or in combination with each other, can be used at concentrations varying from 0.1 to 1000 ppm (by weight), preferably between 1 and 100 ppm (by weight) in the final cosmetic or dermopharmaceutical product.

The peptides of this patent, alone or in combination with each other, can be used in the form of solutions, dispersions, emulsions, or encapsulated in vectors such as macro-, micro- or nano-capsules, lyposomes or chylomicrons, or included in macro-, micro- or nano-particles, or in micro-sponges, or adsorbed or powdered organic polymers, talcs, bentonites and other mineral supports.

The peptides of this patent, alone or in combination with each other, can be used in any galenic form: O/W emulsions and W/O emulsions, milks, lotions, gelifying and thickening, tensioactive and emulsifying polymers, pomades, lotions, capillaries, shampoos, soaps, powders, sticks and pencils, sprays, body oils.

The peptides of this patent, alone or in combination with each other, can be used with any other ingredient conventionally used: extraction and/or synthesis lipids, gelifying and thickening, tensioactive and emulsifying polymers, hydrosoluble or liposoluble active principles, vegetable extracts, tissue extracts, marine extracts, solar filters, antioxidants.

The peptides of this patent, alone or in combination with each other, are used in cosmetic applications to promote healing, hydration and for all skin care, particularly against the formation and worsening of wrinkles and against any consequences of cutaneous aging, natural or accelerated (heliodermia, pollution).

The peptides of this patent, alone or in combination with each other, as well as the cosmetic and dermopharmaceutical compositions containing them, are used for the preparation of a medication to promote healing, hydration and for all skin care, particularly against the formation and worsening of wrinkles and against all the consequences of cutaneous aging, natural or accelerated (heliodermia, pollution).

What is claimed is:

1. Peptides of the general formula $R_1$-X-Thr-Thr-Lys-$(AA)_n$-Y, excluding H-Lys-Thr-Thr-Lys-OH and H-Lys-Thr-Thr-Lys-Ser-OH, and their salts, wherein:

X represents a basic amino acid of D or L orientation selected from the group consisting of lysine, arginine, histidine, ornithine, citruline, sarcosine, and statine, $(AA)_n$ represents a chain of n amino acids wherein n varies from 0 to 5, $R_1$ being as follows:
H;
a fatty acid chain of 2 to 22 carbons, wherein said fatty acid chain is hydroxylated or non-hydroxylated, saturated or unsaturated, linear or branched, sulfurated or non-sulfurated, cyclic or non-cyclic;
a biotin group; or
a protective group selected from the group consisting of benzyloxycarbonyl (Z), terbutyloxycarbonyl (tBoc), fluorenylmethyloxycarbonyl (Fmoc), and allyloxycarbonyl (Alloc) groups, and Y=$OR_2$ or $NR_2R_3$ wherein $R_2$ and/or $R_3$ are a hydrogen atom or an aliphatic or aromatic chain of 1 to 22 carbons, hydroxylated or non-hydroxylated, saturated or unsaturated, linear or branched, sulfurated or non-sulfurated, cyclic or non-cyclic.

2. The peptides according to claim 1, wherein n=1, $R_1$ is a fatty acid chain of 2 to 22 carbons, and Y is OH or $NH_2$.

3. The peptide according to claim 2, wherein X is lysine, $R_1$ is the palmitoyl group, Y is the OH group, and $(AA)_n$ wherein (AA) is serine and n=1.

4. A cosmetic or dermopharmaceutical composition including a peptide or peptides of the general formula $R_1$-X-Thr-Thr-Lys-$(AA)_n$-Y, excluding H-Lys-Thr-Thr-Lys-OH and H-Lys-Thr-Thr-Lys-Ser-OH and their salts, wherein:

X represents a basic amino acid of D or L orientation selected from the group consisting of lysine, arginine, histidine, ornithine, citruline, sarcosine, and statine, $(AA)_n$ represents a chain of n amino acids wherein n varies from 0 to 5, $R_1$ being as follows:
H;
a fatty acid chain of 2 to 22 carbons, wherein said fatty acid chain is hydroxylated or non-hydroxylated, saturated or unsaturated, linear or branched, sulfurated or non-sulfurated, cyclic or non-cyclic;
a biotin group; or
a protective group selected from the group consisting of benzyloxycarbonyl (Z), terbutyloxycarbonyl (tBoc), fluorenylmethyloxycarbonyl (Fmoc), and allyloxycarbonyl (Alloc) groups, and Y=$OR_2$ or $NR_2R_3$ wherein $R_2$ and/or $R_3$ are a hydrogen atom or an aliphatic or aromatic chain of 1 to 22 carbons, hydroxylated or non-hydroxylated, saturated or unsaturated, linear or branched, sulfurated or non-sulfurated, cyclic or non- cyclic.

5. A cosmetic or dermopharmaceutical composition containing a peptide or peptides according to claim 2.

6. A cosmetic or dermopharmaceutical composition containing a peptide according to claim 3.

7. The cosmetic or dermopharmaceutical composition according to claim 4, wherein the peptide(s) is/are obtained by synthesis, by fermentation, or by extraction of proteins of vegetable origin.

8. The cosmetic or dermopharmaceutical composition according to claim 4, wherein the peptide(s) is/are at concentrations varying between 0.1 and 1000 ppm by weight based on the total weight of said composition.

9. The cosmetic or dermopharmaceutical composition according to claim 8, wherein said amount of said peptide(s) is between 1 and 100 ppm by weight based on the total weight of said composition.

10. The cosmetic or dermopharmaceutical composition according to claim 4, wherein
   a) said peptide is encapsulated in a vector selected from the group consisting of macro-capsules, micro-capsules, nano-capsules, liposomes, chylomicrons and microsponges, or
   b) said peptide is absorbed on a material selected from the group consisting of powdered organic polymers, talcs, bentonites, and other mineral supports.

11. The cosmetic or dermopharmaceutical composition according to claim 4, wherein said composition is in a galenic form selected from the group consisting of O/W emulsions, W/O emulsions, milks, lotions, pomades, lotions, shampoos, soaps, powders, sticks, pencils, sprays and body oils.

12. The cosmetic or dermopharmaceutical composition according to claim 4, further comprising ingredients selected from the group consisting of extracted lipids, synthetic lipids, gelifying polymers, thickening polymers, tensioactive polymers, emulsifying polymers, hydrosoluble active principles, liposoluble active principles, vegetable extracts, tissue extracts, marine extracts, solar filters and antioxidants.

13. A method of inducing concommital synthesis of collagen and glycosaminoglycans in an individual, comprising administering to said individual an effective amount of a peptide according to claim 1.

14. A method of inducing concommital synthesis of collagen and glycosaminoglycans in an individual, comprising administering to said individual an effective amount of a composition according to claim 4.

15. A method of inhibiting the development of wrinkles associated with advancing age, or with sun-induced or pollution-induced skin aging, comprising administering to an individual, by topical application, the composition according to claim 4.

16. A method of inhibiting the development of wrinkles associated with advancing age, or with sun-induced or pollution-induced skin aging, comprising administering to an individual, by topical application, the composition according to claim 10.

* * * * *